United States Patent
Kawaminami et al.

(10) Patent No.: US 11,852,630 B2
(45) Date of Patent: Dec. 26, 2023

(54) IMMUNOCHROMATOGRAPHIC TEST PIECE

(71) Applicant: TOYOBO CO., LTD., Osaka (JP)

(72) Inventors: Hiroshi Kawaminami, Tsuruga (JP); Yuji Tsuji, Otsu (JP); Keizo Yoneda, Otsu (JP)

(73) Assignee: TOYOBO CO., LTD., Osaka (JP)

( * ) Notice: Subject to any disclaimer, the term of this patent is extended or adjusted under 35 U.S.C. 154(b) by 273 days.

(21) Appl. No.: 15/767,468

(22) PCT Filed: Oct. 13, 2016

(86) PCT No.: PCT/JP2016/080369
§ 371 (c)(1),
(2) Date: Apr. 11, 2018

(87) PCT Pub. No.: WO2017/065213
PCT Pub. Date: Apr. 20, 2017

(65) Prior Publication Data
US 2018/0299455 A1    Oct. 18, 2018

(30) Foreign Application Priority Data
Oct. 16, 2015   (JP) .................................. 2015-204680

(51) Int. Cl.
*G01N 33/543*   (2006.01)
*G01N 33/76*    (2006.01)

(52) U.S. Cl.
CPC . *G01N 33/54388* (2021.08); *G01N 33/54393* (2013.01); *G01N 33/76* (2013.01); *G01N 2333/59* (2013.01)

(58) Field of Classification Search
CPC ........... G01N 33/558; G01N 33/54393; G01N 33/543; G01N 33/54386–54391;
(Continued)

(56) References Cited

U.S. PATENT DOCUMENTS 5,132,242 A * 7/1992 Cheung .................... B01J 13/20
436/501
5,834,319 A * 11/1998 Ekins ..................... G01N 33/58
436/518
(Continued)

FOREIGN PATENT DOCUMENTS

CN   102192983 A   9/2011
CN   102539755 A   7/2012
(Continued)

OTHER PUBLICATIONS

Ma et al., CN102192983B (published 2013), machine translations as retrieved from https://worldwide.espacenet.com/patent/search/family/044601452/publication/CN102192983B?q=pn%3DCN102192983B (33 pages total).*

(Continued)

*Primary Examiner* — Christopher L Chin
(74) *Attorney, Agent, or Firm* — Wenderoth, Lind & Ponack, L.L.P.

(57) ABSTRACT

An immunochromatographic test piece is provided containing a control line detection reagent that is not affected by the concentration of an analyte to be detected. The immunochromatographic test piece is for quantifying an analyte in a biological sample, and includes (a) a conjugation pad impregnated with a detection reagent that specifically binds to the analyte, and a control line detection reagent; and (b) a porous membrane pad on which an antibody for capturing the analyte is immobilized upstream, and an antibody for capturing specifically the control line detection reagent is immobilized downstream.

4 Claims, 4 Drawing Sheets
Specification includes a Sequence Listing.

(58) Field of Classification Search
CPC ....... G01N 33/54387; G01N 33/54388; G01N 33/54389; G01N 33/76; G01N 2333/59; G01N 33/53; G01N 2035/00108; G01N 2035/00118; G01N 2035/00128; G01N 2021/7759; G01N 21/8483; G01N 2021/8494; B01L 3/5023; B01L 2300/0825; Y10S 435/97
USPC ....... 422/400, 401, 420, 421, 425, 426, 430; 435/287.7, 287.9, 970, 805, 810; 436/169, 170, 514, 518, 525, 530, 531, 436/810

See application file for complete search history.

(56) References Cited

U.S. PATENT DOCUMENTS

| | | | |
|---|---|---|---|
| 2006/0183173 A1* | 8/2006 | Kuroita | G01N 33/54393 435/7.92 |
| 2006/0199278 A1* | 9/2006 | Leclipteux | G01N 33/558 436/514 |
| 2008/0176340 A1* | 7/2008 | Soldo | G01N 33/543 436/518 |
| 2009/0246886 A1 | 10/2009 | Buck | |
| 2010/0209295 A1* | 8/2010 | Self | G01N 33/54386 422/423 |
| 2013/0164858 A1 | 6/2013 | Nazareth et al. | |
| 2013/0244314 A1 | 9/2013 | Yuki et al. | |
| 2014/0363833 A1 | 12/2014 | Bhatia et al. | |
| 2015/0301038 A1* | 10/2015 | Yokokawa | C07K 14/765 436/501 |

FOREIGN PATENT DOCUMENTS

| | | | |
|---|---|---|---|
| CN | 102680692 A | 9/2012 | |
| CN | 203 732 547 U | 7/2014 | |
| EP | 2728356 A1 * | 5/2014 | ........... G01N 33/553 |
| EP | 2853894 A1 | 4/2015 | |
| JP | 11-118801 A | 4/1999 | |
| JP | 2006-67979 A | 3/2006 | |
| JP | 2008-164300 A | 7/2008 | |
| JP | 2008-292270 A | 12/2008 | |
| JP | 2010-14631 A | 1/2010 | |
| JP | 2010-101673 A | 5/2010 | |
| JP | 2010-525356 A | 7/2010 | |
| JP | 2010-256012 A | 11/2010 | |
| JP | 2012-251789 A | 12/2012 | |
| JP | 2013-205335 A | 10/2013 | |
| WO | 2008/129302 A1 | 10/2008 | |
| WO | 2014/197840 A1 | 12/2014 | |

OTHER PUBLICATIONS

Vogler, E.A. "Protein adsorption in three dimensions", Biomaterials vol. 33, Issue 5, 2012, pp. 1201-1237, https://doi.org/10.1016/j.biomaterials.2011.10.059.*

Lee, L. et al., "A Low-Cost, High-Performance System for Fluorescence Lateral Flow Assays", Biosensors, Oct. 21, 2013, vol. 3, No. 4. pp. 360-373, XP55424832; cited in EESR dated Apr. 17, 2019.

"Lateral Flows Tests Involving Fluorescent Dyes", ip.com Journal, Jun. 22, 2015, XP013167894; cited in EESR dated Apr. 17, 2019.

Extended (supplementary) European Search Report dated Apr. 17, 2019, issued in counterpart EP Application No. 16855466.5. (6 pages).

Office Action dated Mar. 18, 2020, issued in counterpart EP Application No. 16 855 466.5 (5 pages).

International Search Report dated Dec. 20, 2016, issued in Counterpart of International Application No. PCT/JP2016/080369 (2 pages).

Office Action dated Oct. 15, 2019, issued in counterpart CN Application No. 201680060111.9, with English translation (summary). (12 pages).

"Blocking Peptide Fragment", https://www.docin.com/p-875438329.html, pp. 1-5, Jul. 28, 2014.

* cited by examiner

| hCG (IU/L) | 1 | 10 | 100 | 1000 | Average | Standard deviation | Coefficient of variation |
|---|---|---|---|---|---|---|---|
| Reflection absorbance (mAbs) | 298.6 | 314.86 | 307.36 | 299.68 | 305.13 | 6.6 | 2.15 |

| hCG (IU/L) | 1 | 10 | 100 | 1000 | Average | Standard deviation | Coefficient of variation |
|---|---|---|---|---|---|---|---|
| Reflection absorbance (mAbs) | 206 | 190.3 | 170.9 | 79.7 | 161.73 | 49.0 | 30.3 |

IMMUNOCHROMATOGRAPHIC TEST PIECE

A sequence listing in electronic (ASCII text file) format is incorporated herein by reference. The name of the ASCII text file is "2020-2709-seq-listing.txt"; the file was created on Mar. 22, 2022; the size of the file is 4 KB.

TECHNICAL FIELD

The present invention relates to a method for detecting an analyte contained in a biological sample by immunochromatography, a kit for the detection, and a method for producing the kit.

BACKGROUND ART

Immunochromatography is an immunoassay comprising preparing a porous support on which an antibody that specifically binds to an analyte is immobilized, and developing a biological sample from one end portion of the porous support while allowing the biological sample to migrate in the porous support by capillary action, during which the analyte is labeled and bound to the antibody by an immune response, whereby the analyte is accumulated over time and color development occurs locally, thus determining the presence or absence of the analyte in the biological sample.

Advantages of immunochromatography are, for example, that it is easy to operate, and visually assessable. In vitro diagnostics utilizing these advantages, such as pregnancy test agents and influenza diagnostic agents, have been widely used around the world, and have been attracting attention as POCT (Point-of-Care Testing) (Patent Literature (PTL) 1).

POCT refers to clinical testing that is conducted by a medical care provider at a subject's side. Unlike clinical tests performed in central laboratories of large hospitals or the like, test results of POCT can be instantly obtained on the spot. Accordingly, the need therefor is growing in medical settings.

Conventional immunochromatography is usually visual assessment (qualitative assessment). In recent years, however, by utilizing chromatographic readers or like devices for measuring the intensity of color development, techniques for quantifying the concentration of an analyte in a biological sample are being developed.

A representative technique for such quantification is the sandwich method. The sandwich method utilizes two kinds of antibodies for different epitopes of an analyte. The first antibody is used as a detection reagent sensitized with detection particles, such as gold colloid, colored latex, or fluorescent particles. The second antibody is used as a capture antibody immobilized on one end portion of a porous support to perform a test line measurement. In addition, an antibody that specifically binds to a detection antibody is immobilized on the other end portion of the porous support, and used for a control line measurement. The analyte contained in a biological sample is developed from one end of the porous support, and migrates while forming an immunocomplex with a detection antibody. The immunocomplex comes into contact with and is captured by a capture antibody on the test line, so that the test line is colored. The free detection reagent that did not form an immunocomplex with the analyte passes through the test line is captured by an antibody on the control line, so that the control line is colored. The concentration of the analyte can be determined by measuring the intensity of color development on these lines using a device such as a chromatographic reader.

Conventional immunochromatography uses the same detection reagent for test line detection and control line detection. This causes a problem that the intensity of color development on the control line varies due to the influence of the analyte concentration. Specifically, the following problem arises. When an analyte is present in a high concentration in a biological sample, a large amount of detection particles form an immunocomplex with the analyte, and the immunocomplex is captured on the upstream test line; accordingly, the intensity of color development on the test line is high. On the other hand, since the amount of free detection reagent is reduced, the intensity of color development on the control line is low. When an analyte is present in a low concentration in a biological sample, a small amount of detection particles form an immunocomplex with the analyte, and a large amount of free detection particles are captured on the control line. As a result, the intensity of color development on the control line is high.

In the quantification of immunochromatography, the control line may be used to measure the amount of detection reagent flowing into the porous support. Therefore, when a specific amount of detection reagent is developed in a porous support, the intensity of color development is desirably always constant. If the intensity of color development on the control line varies due to the influence of the analyte concentration as described above, it may severely affect measurement accuracy.

CITATION LIST

Patent Literature

PTL 1: JP2006-67979A

SUMMARY OF INVENTION

Technical Problem

In view of the above problem, an object of the present invention is to provide a control line detection reagent as a detection reagent that is not affected by the concentration of an analyte to be detected; and thereby provide an immunochromatographic analysis method with higher accuracy than conventional methods, an immunochromatographic test piece and a kit using the immunochromatographic analysis method, and a method for producing the kit.

Solution to Problem

The present inventors conducted extensive research to achieve the above object. As a result, the inventors found that when a detection reagent comprising a control line detection reagent is used as a detection reagent for detecting a control line, the intensity of color development on the control line can be made more constant without being affected by the concentration of an analyte in a biological sample. The inventors performed further research based on this finding and accomplished inventions, such as an immunochromatographic test piece comprising the control line detection reagent; a method for producing the test piece; and a method for quantifying an analyte in a biological sample by using the immunochromatographic test piece.

Specifically, representative inventions of the present invention are as follows.

(1) An immunochromatographic test piece for quantifying an analyte in a biological sample,
the immunochromatographic test piece comprising
a) a conjugation pad impregnated with a detection reagent that specifically binds to the analyte, and a control line detection reagent, and
b) a porous membrane pad on which an antibody for capturing the analyte is immobilized upstream, and an antibody for specifically capturing the control line detection reagent is immobilized downstream.
(2) The immunochromatographic test piece according to (1), wherein the control line detection reagent comprises detection particles having a biotin-labeled protein bound thereto.
(3) The immunochromatographic test piece according to (2), wherein the protein is a microorganism-derived or animal-derived protein.
(4) The immunochromatographic test piece according to (3), wherein the microorganism-derived protein is a blocking peptide fragment.
(5) The immunochromatographic test piece according to (3), wherein the animal-derived protein is bovine serum albumin or casein.
(6) The immunochromatographic test piece according to any one of (1) to (5), wherein the antibody for specifically capturing the control line detection reagent is an antibiotin antibody.
(7) A method for quantifying an analyte in a biological sample, the method comprising using the immunochromatographic test piece according to any one of (1) to (6).
(8) An immunochromatographic analysis kit comprising the immunochromatographic test piece according to any one of (1) to (6), a sample diluent, and an analyzing device.
(9) A method for producing the immunochromatographic test piece according to any one of (1) to (6).

Advantageous Effects of Invention

According to the immunochromatographic test piece of the present invention, the intensity of color development on the control line can be made more constant without varying depending on the concentration of an analyte in a biological sample. Therefore, an immunochromatographic test piece with high measurement accuracy can be provided.

DESCRIPTION OF EMBODIMENTS

One embodiment of the immunochromatographic test piece of the present invention is described. An embodiment of the present invention is an immunochromatographic test piece comprising a detection reagent that specifically binds to an analyte, and a control line detection reagent.

Control Line Detection Reagent

The control line detection reagent used in the present invention comprises detection particles having a biotin-labeled protein bound thereto. The biotin-labeling method is not particularly limited. For example, a binding method using the N-hydroxysuccinimide method can be used. Examples of detection particles include, but are not limited to, gold colloid, latex particles, fluorescent particles, and the like. The method of binding a biotin-labeled protein and detection particles is not particularly limited. For example, physical adsorption by hydrophobic bonding or conjugation through covalent bonding can be used.

Protein

The type of protein used as the biotin-labeled protein is not particularly limited. For example, microorganism-derived proteins and animal-derived proteins are preferable. More preferably, the microorganism-derived protein is a Blocking Peptide Fragment, and the animal-derived protein is bovine serum albumin or casein. Such proteins to be used may be commercially available products, or otherwise produced by known methods. The molecular size is also not particularly limited. The protein preferably has an average molecular weight of 100 kDa or less. In general, as the molecular size of a protein is smaller, the amount of the protein bound per particle of detection particles increases, which leads to high performance, such as sensitivity.

Detection Particles

The type of detection particles is not particularly limited. For example, coloring particles or fluorescent particles can be used. Examples of coloring particles include metal particles and latex particles. Examples of metal particles include gold colloid, silver colloid, platinum colloid, and the like. The particle size of metal particles is not particularly limited, and is preferably 1 to 100 nm, more preferably 20 to 80 nm, and still more preferably 40 to 60 nm. Examples of latex particles include particles of polystyrene, polymethyl methacrylate, acrylic acid polymers, or like materials. The particle size of the latex particles is not particularly limited, and is preferably 25 to 500 nm, more preferably 50 to 250 nm, and still more preferably 80 to 200 nm. Examples of fluorescent particles include, but are not limited to, particles of polystyrene, polymethyl methacrylate, polyvinyl toluene, silica, or like materials. Examples of fluorescent dyes include, but are not limited to, FITC (fluorescein isothiocyanate), rhodamine B derivatives, hydroxycoumarin, and the like. Among these, gold colloid and latex particles, which are versatile and highly visible, are preferably used.

The N-Hydroxysuccinimide Method

The biotin-labeling method for a biotin-labeled protein is not particularly limited. For example, the N-hydroxysuccinimide method can be used. When the N-hydroxysuccinimide method is used, the carboxyl group of biotin is subjected to a condensation reaction with an N-hydroxyamine compound in the presence of a dehydration condensation agent, and selectively activated to label a protein via an amide bond with an amino group of the protein.

N-Hydroxyamine Compound

The N-hydroxyamine compound used in the condensation reaction is not particularly limited. Examples of N-hydroxyamine compounds include N-hydroxysuccinimide, N-hydroxynorbornene-2,3-dicarboxylic acid imide, 2-hydroxyimino-2-cyanoacetic acid ethyl ester, 2-hydroxyimino-2-cyanoacetamide, N-hydroxypiperidine, N-hydroxyphthalimide, N-hydroxyimidazole, N-hydroxymaleimide, and the like. These compounds may be used singly, or in a combination of two or more. Among these, N-hydroxysuccinimide (hereinafter sometimes referred to as NHS) is preferable because it is relatively inexpensive and easily available, and has been proven effective in the fields of peptide synthesis and the like.

Dehydration Condensation Agent

Examples of the dehydration condensation agent used in the condensation reaction include, but are not limited to, 1-ethyl-3-dimethylaminopropyl carbodiimide hydrochloride, 1-cyclohexyl-(2-morphonyl-4-ethyl)-carbodiimide·meso-p-toluene sulfonate, and the like. Among these, 1-ethyl-3-dimethylaminopropyl carbodiimide hydrochloride (hereinafter sometimes referred to as EDC·HCl) is preferable because it has been used as a general-purpose water-soluble condensation agent in the fields of peptide synthesis and the like.

Amount of Biotin Introduced

The amount of biotin introduced into the biotin-labeled protein can be controlled by adjusting the molar ratio of the protein and biotin. A larger amount of biotin introduced is preferable in order to enhance performance, such as sensitivity. More specifically, the number of moles of biotin per mole of the protein is preferably 1.0 mol or more, more preferably 5.0 mol or more, and most preferably 10.0 mol or more. The molar ratios mentioned above are merely examples. The molar ratio may be appropriately increased or decreased according to the type of protein and actual sensitivity.

Binding of Biotin-Labeled Protein and Detection Particles

The method of binding the biotin-labeled protein and detection particles is not particularly limited. For example, physical adsorption via hydrophobic bonding or conjugation via covalent bonding can be used. In hydrophobic bonding, a biotin-labeled protein is directly bound to the surface layer of detection particles. Therefore, treatment at a pH near the isoelectric point of the biotin-labeled protein is preferable. In covalent bonding, the binding method may vary depending on the functional group on the surface of detection particles. For example, when the functional group present on the surface of detection particles is an amino group, binding can be formed by the N-hydroxysuccinimide method.

The reaction temperature is not particularly limited. The lower limit of the reaction temperature is preferably 10° C., and more preferably 20° C. or more. The upper limit of the reaction temperature is preferably 50° C., and more preferably 40° C. or less. The reaction time may vary depending on the reaction temperature, and is preferably 1 hour or more and 24 hours or less, and more preferably 2 hours or more and 12 hours or less.

The unreacted N-hydroxyamine compound and dehydration condensation agent contained in the reaction mixture can be easily separated from an aqueous solvent by, for example, filtration or centrifugation.

Detection Reagent that Specifically Binds to Analyte

The detection reagent that specifically binds to the analyte is detection particles that have bound thereto an antibody capable of binding to the analyte in a biological sample (hereinafter sometimes referred to as a detection antibody). The detection antibody to be used may vary depending on the kind of analyte. The detection antibody to be used may be a commercially available product, or otherwise produced by a known method. The molecular size is also not particularly limited.

Antibody for Capturing Analyte

The antibody for capturing an analyte (hereinafter sometimes referred to as the capture antibody) may be a commercially available product, or otherwise produced by a known method. An antibody that recognizes a site of the analyte that is distinct from the site recognized by a detection antibody is preferably used as the capture antibody. The molecular size is also not particularly limited. Examples of capture antibodies for measuring human chorionic gonadotropin include Anti-hCG 1646157 (V-24), Human (Rabbit) (produced by Santa Cruz Biotechnology, Inc.), Anti-hCG/Chorionic Gonadotropin, Human (Mouse) (produced by LifeSpan BioSciences, Inc.), Anti-CGB/hCG β, Human (Mouse) (produced by LifeSpan BioSciences, Inc.), Anti-Chorionic Gonadotropin, Human (Rabbit) (produced by EY Laboratories, Inc.), Anti-β-HCG, Human (Mouse) (produced by Boster Immunoleader), Anti-CG α (α-HCG), Human (Rabbit) (produced by R&D Systems Inc.), and the like.

Antibody that Captures Control Line Detection Reagent

The antibody that captures a control line detection reagent specifically refers to an antibody that captures biotin (hereinafter referred to as the antibiotin antibody). The antibiotin antibody to be used may be a commercially available product, or may be produced by a known method. The molecular size is also not particularly limited. Examples of antibiotin antibodies include Anti-Biotin antibody (produced by GeneTex, Inc.), Anti-Biotin, Goat-Poly (produced by Bethyl Laboratories, Inc.), IgG Fraction Monoclonal Mouse Anti-Biotin (produced by Iwai Chemicals Company), and the like.

Porous Membrane Pad

The capture antibody is immobilized on the upstream side (test line) of a porous membrane pad, whereas an antibiotin antibody is immobilized on the downstream side (control line) of the porous membrane pad to produce a porous membrane pad that can be used in immunochromatography and the like. These antibodies can be easily immobilized on porous membrane pads that are generally used in immunochromatography etc. Examples of materials of such porous membrane pads include, but are not limited to, cellulose, cellulose derivatives, nitrocellulose, cellulose acetate, polyurethane, polyester, polyethylene, polyvinyl chloride, polyvinylidene fluoride, nylon, and the like. Membranes, fabrics, fibrous or nonwoven matrices, and the like composed of such materials are preferable. Cellulose derivative membranes are preferable, and nitrocellulose membranes are more preferable.

Figure 1:
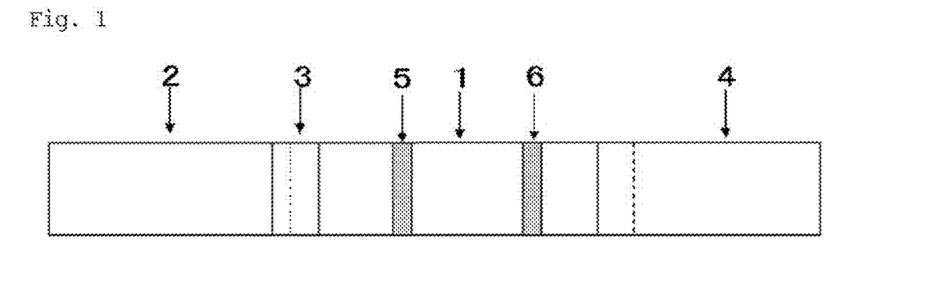
FIG. 1 is a top view of an example of the immunochromatographic test piece used in the present invention.

Subsequently, an example of the immunochromatographic test piece of the present invention is described with reference to the accompanying drawings. In FIG. 1, 1 is a porous membrane pad; 2 is a sample pad; 3 is a conjugation pad; 4 is an absorbent pad; 5 is an immobilization site at which a capture antibody is immobilized (test line); 6 is an immobilization site at which an antibiotin antibody is immobilized (control line); and 7 is an adhesive sheet.

An example of the porous membrane pad shown in FIG. 1 is a nitrocellulose membrane having a strip shape with a width of 4 mm and a length of 60 mm. The conjugation pad of an immunochromatographic test piece is impregnated with a detection reagent, which specifically binds to an analyte, and a control line detection reagent. A test line 5 having a capture antibody immobilized thereto is formed at a location about 10 mm from the end portion on the starting side of chromatographic development of a nitrocellulose membrane. A control line 6 having an antibiotin antibody immobilized thereto is formed at a location about 15 mm from the end portion on the starting side of chromatographic development of the nitrocellulose membrane.

The immunochromatographic test piece as shown in FIG. 1 can be produced in the following manner. A porous membrane pad 1 is adhered to a substantially middle position of an adhesive sheet 7. A sample pad 2 and a conjugation pad 3 are joined to one end portion of the porous membrane pad 1 in such a manner that the conjugation pad 3 is partially overlapped with the porous membrane pad 1, whereas an absorbent pad 4 is joined to the other end portion of the porous membrane pad 1 in such a manner that the absorbent pad 4 is overlapped with the porous membrane pad 1.

The sample pad 2 is not particularly limited as long as it is made of a material that can rapidly absorb and develop a biological sample. Examples of the sample pad 2 include cellulose filter paper, cellulose non-woven fabrics, or like pads comprising a porous synthetic resin, such as polyethylene or polypropylene. Among these, filter paper is preferable.

The conjugation pad 3 is not particularly limited as long as it can maintain a detection reagent in a dry state, and can rapidly release the detection reagent while a biological sample is developed. Examples of the conjugation pad 3 include glass fiber filters, cellulose filters, polyester non-woven fabrics, and the like. Glass fibers are more preferable.

The absorbent pad 4 is not particularly limited as long as it can rapidly absorb and maintain a biological sample. Examples of the absorbent pad 4 include cellulose filter papers, cellulose non-woven fabrics, or like pads comprising a porous synthetic resin, such as polyethylene or polypropylene. Among these, cellulose filter paper is preferable.

The immunochromatographic test piece may be accommodated in an appropriate plastic case in which an opening for injecting a biological sample, and openings for quantifying the amount of captured detection particles are provided above the sample pad 2, test line 5, and control line 6.

Method for Producing Immunochromatographic Test Piece

The method for producing the immunochromatographic test piece of the present invention is not particularly limited. For example, the conjugation pad can be produced by uniformly applying a certain amount of a detection reagent to strip-shaped glass fibers, and then drying in a thermostat bath at a suitable temperature for a fixed period of time. The capture antibody and the antibiotin antibody may be applied in fixed amounts to a porous membrane pad to form lines thereon. The method for application to the membrane pad is not particularly limited. For example, a commercially available immunochromatography dispenser can be used. The amounts of the capture antibody and antibiotin antibody applied are not particularly limited, and are preferably 10 μl or less, more preferably 8 μl or less, even more preferably 6 μl or less, per 10 cm of the line length. The lower limit is preferably 4 μl or more. The concentrations of the capture antibody and antibiotin antibody are not particularly limited, and are preferably 2.0 to 0.1 mg/ml, more preferably 1.8 to 0.2 mg/ml, and even more preferably 1.6 to 0.3 mg/ml.

The capture antibody and antibiotin antibody applied to the membrane pad can be very easily immobilized on the membrane pad merely by drying. The drying temperature is not particularly limited, and is preferably 20° C. to 80° C., more preferably 30 to 70° C., and even more preferably 40 to 60° C. The drying time varies according to the drying temperature, and is usually 5 to 120 minutes, and preferably 10 to 60 minutes.

In the present invention, the immunochromatographic analysis kit comprises a sample diluent for pretreatment or dilution of a biological sample, an immunochromatographic test piece, and an analyzing device.

Method for Measuring Analyte Using Immunochromatographic Test Piece

The method of measurement using the immunochromatographic test piece is not particularly limited. For example, the following method can be used. First, if necessary, a biological sample is mixed with an appropriate developing solvent so as to obtain a mixture that can be developed chromatographically. The mixture is then injected onto (added dropwise to) the sample pad 2. The mixture passes through the sample pad 2, and is developed in the conjugation pad 3. While the biological sample dissolves a detection reagent and a control line reagent impregnated in the conjugation pad 3, an analyte and the detection reagent form an immunocomplex, and the mixture is developed in a porous membrane pad. The mixture then flows toward the absorbent pad side 4 due to capillary action. When the mixture reaches the test line 5 on the porous membrane pad, the immunocomplex is captured by a capture antibody and accumulated, so that the test line 5 is colored. The developing solvent containing a control line detection reagent passes through the test line 5, and reaches the control line 6. The control line detection reagent is captured by an antibiotin antibody and accumulated, so that the control line 6 is colored. The other developing solvent is finally absorbed by the absorbent pad. The concentration of the analyte can be determined by measuring the intensity of color development on the test line 5 and the control line 6 using, for example, an immunochromatographic reader.

Intensity of Color Development on the Control Line

The intensity of color development on the control line is not particularly limited as long as it is at color intensity levels that can be observed with the naked eye or detected by using an immunochromatographic reader. The intensity of color development is preferably in the range of 10 mAbs to 500 mAbs, more preferably 50 mAbs to 450 mAbs, and even more preferably 100 mAbs to 400 mAbs. The intensity of color development is preferably constant regardless of the concentration of the analyte to be detected. More specifically, the coefficient of variation in intensity of color development is preferably 20% or less, more preferably 10% or less, and even more preferably 5% or less.

The coefficient of variation can be calculated by following Formulas 1 and 2.

$$\text{Standard deviation} = \sqrt{\frac{\text{Sum of (Measurement value} - \text{Average value)}^2}{\text{Number of data}}} \quad \text{Formula 1}$$

$$\text{Coefficient of variation (\%)} = \text{Standard deviation/Average value} \times 100 \quad \text{Formula 2}$$

EXAMPLES

The present invention is described below in detail with reference to Examples. However, it should be understood that the present invention is not limited to these Examples.

Example 1

Preparation of hCG Detection Reagent

50 μl of 10 mM Tris-HCl having a pH of 9.2 was added to 125 μl of a gold colloid solution ($OD_{520}$=12) (WRGH1, produced by Winered Chemical Co., Ltd.), and stirred by vortexing. A commercially available anti-hCG monoclonal antibody (product name: Anti CGB/hCG β, Human (Mouse), Product Number: LS-C196902-100, produced by LifeSpan Biosciences, Inc.) was adjusted to a concentration of 0.1 mg/ml using 10 mM Tris-HCl. After 100 μl of the anti-hCG monoclonal antibody solution was added to the gold colloid solution and stirred by vortexing, the resulting mixture was allowed to stand at room temperature for 15 minutes. After 200 μl of an aqueous solution of 0.3 wt % Blocking Peptide Fragment (produced by Toyobo Co., Ltd.) (hereinafter sometimes referred to as BPF)(SEQ ID NO: 1)+1.0 wt % PEG20000 (produced by Santa Cruz Biotechnology Inc.) (hereinafter sometimes referred to as PEG) was added and stirred by vortexing, the resulting mixture was allowed to stand at room temperature for 15 minutes. The mixture was then centrifuged at 7000 rpm for 10 minutes, and the supernatant was removed. After 200 μl of an aqueous solution of 0.3 wt % BPF+1.0 wt % PEG was added and stirred by vortexing, the mixture was allowed to stand at room temperature for 15 minutes. The mixture was centrifuged at 7000 rpm for 10 minutes, and the supernatant was removed. After 1 ml of an aqueous solution of 0.3 wt % BPF+5.0 wt % D(+)-trehalose (produced by Nacalai Tesque, Inc.) was added and stirred by vortexing, the resulting mixture was allowed to stand at room temperature for 15 minutes.

Preparation of Control Line Detection Reagent 3.15 mg of D-biotin (produced by Nacalai Tesque, Inc.) was dissolved in 72 μl of distilled water. 10 mg of 1-ethyl-3-(3-dimethylaminopropyl)carbodiimide (produced by Nacalai Tesque, Inc.) and 10 mg of N-hydroxysuccinimide (produced by Nacalai Tesque, Inc.) were dissolved in 100 μl of distilled water. D-biotin solution was added thereto, and the resulting mixture was gently stirred at room temperature for 1 hour. After 80 μl of a 3 wt % BPF solution was added to the solution, the resulting mixture was allowed to stand at room temperature for 30 minutes to prepare a biotin-labeled BPF solution. Subsequently, 450 μl of 10 mM Tris-HCl having a pH of 9.2 was added to 50 μl of a gold colloid solution ($OD_{520}$=12), and stirred by vortexing. Further, after 15 μl of a biotin-labeled BPF solution was added to the gold colloid solution and stirred by vortexing, the resulting mixture was allowed to stand at room temperature for 15 minutes. After 200 μl of an aqueous solution of 0.3 wt % BPF+1.0 wt % PEG20000 (produced by Santa Cruz Biotechnology Inc.) (hereinafter sometimes referred to as PEG) was added and stirred by vortexing, the resulting mixture was allowed to stand at room temperature for 15 minutes. The mixture was then centrifuged at 7000 rpm for 10 minutes, and the supernatant was removed. After 200 μl of an aqueous solution of 0.3 wt % BSA+1.0 wt % PEG was added and stirred by vortexing, the resulting mixture was allowed to stand at room temperature for 15 minutes. The resulting mixture was centrifuged at 7000 rpm for 10 minutes, and the supernatant was removed. After 1 ml of an aqueous solution of 0.3 wt % BPF+5 wt % D(+)-trehalose (produced by Nacalai Tesque, Inc.) was added and stirred by vortexing, the mixture was allowed to stand at room temperature for 15 minutes.

Preparation of Porous Membrane Pad for hCG Detection

A 0.5 mg/ml solution of an anti-hCG monoclonal antibody (product name: Anti-Chorionic Gonadotropin, Human (Rabbit), product number: AT-2601-2, EY Laboratories, Inc.) (50 mM $KH_2PO_4$, pH 7.0+5 wt % sucrose) was applied in an amount of about 1.0 μl/cm to a site located about 10 mm from one end portion (the upstream side) of a nitrocellulose membrane (trade name: Hi-Flow Plus HF 120 (produced by Merck Millipore Co., Ltd.)) having a size of 25 mm×150 mm so as to form a test line with a width of about 1 mm using an immunochromatography dispenser. Subsequently, a 1.0 mg/ml solution of an antibiotin monoclonal antibody (product name: Anti-Biotin antibody, product number: GTX44344, produced by GeneTex, Inc.) (50 mM $KH_2PO_4$, pH 7.0+5 wt % sucrose) was applied in an amount of about 1.0 μl/cm to a site located about 15 mm from one end portion (the upstream side) of the nitrocellulose membrane so as to form a control line with a line width of about 1 mm using an immunochromatography dispenser. The resulting membrane was then dried at 50° C. for 30 minutes.

Production of the Conjugation Pad for hCG Measurement 1.0 ml of a mixture of the hCG detection reagent and the control line detection reagent (mixing ratio 1:1) was uniformly applied to a conjugation pad with a size of 10 mm×150 mm (trade name: SUREWICK (produced by Merck Millipore Co., Ltd.)). The resulting pad was then dried under reduced pressure at room temperature in a desiccator overnight to prepare a conjugation pad for hCG measurement impregnated with an hCG detection reagent and a control line detection reagent.

Production of Test Piece for hCG Measurement

A test piece for hCG measurement was produced in a side-by-side arrangement, which is generally used in immunochromatography. Specifically, a sample pad (trade name: SUREWICK (produced by Merck Millipore Co., Ltd.)), a conjugation pad (trade name: SUREWICK (produced by Merck Millipore Co., Ltd.)), a nitrocellulose membrane (trade name: Hi-Flow Plus HF 120 (produced by Merck Millipore Co., Ltd.)), and an absorbent pad (trade name: SUREWICK (produced by Merck Millipore Co., Ltd.)) were connected in series with one another. Subsequently, the resulting product was cut with a cutter into a test piece having a width of about 4 mm and a length of about 60 mm.

Preparation of hCG Sample

A commercially available hCG antigen was diluted with 50 mM $KH_2PO_4$ with a pH of 7.2+1.0 wt % BSA+0.1 wt % $NaN_3$ to prepare hCG samples having concentrations of 1 IU/L, 10 IU/L, 100 IU/L, and 1,000 IU/L.

hCG Measurement

Figure 2:
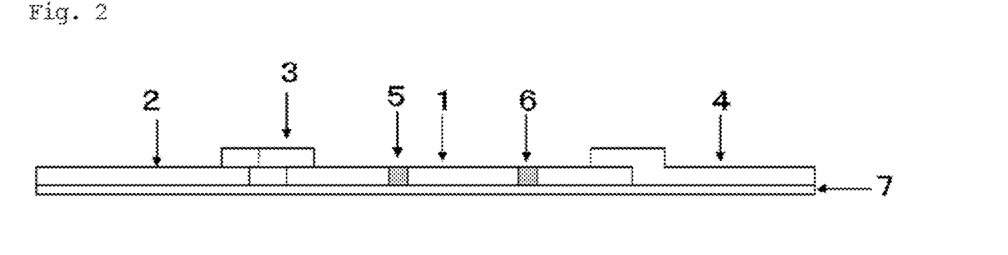
FIG. 2 is a side view of the example of the immunochromatographic test piece used in the present invention.

The produced test pieces for hCG measurement were placed on a horizontal stand. Subsequently, 40 μl each of the 4 levels of hCG samples prepared were pipetted out and added dropwise to sample pads of the test pieces. FIG. 2 is a photograph taken 10 minutes after the samples were added dropwise. The intensity of color development on the test lines increased depending on the hCG concentration. The intensity of the color development on the control lines was not affected by the hCG concentration, and the coefficient of variation in intensity of color development was 2.15%.

Quantification of hCG

Figure 3:
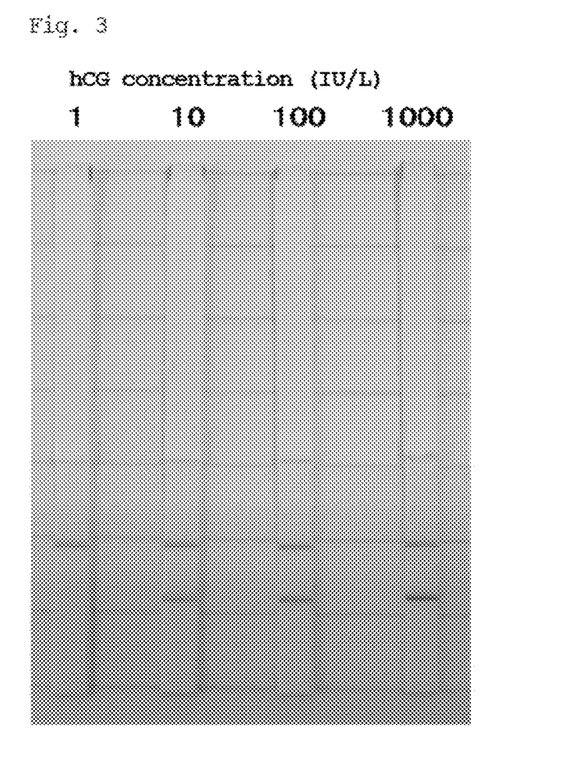
FIG. 3 is a photograph of the results obtained by measuring human chorionic gonadotropin (hCG) using immunochromatographic test pieces of the present invention.

The intensity of color development on the test pieces for hCG measurement was measured using an immunochromatographic reader. C10060-10 (produced by Hamamatsu Photonics, K.K.) was used as the immunochromatographic reader. FIG. 3 shows the results. The test lines were confirmed to have a linear reflection absorbance dependent on the hCG concentration. The reflection absorbance of the control line was confirmed to be about 300 mAbs, and unaffected by the hCG concentration.

Comparative Example 1

Preparation of Porous Membrane Pad for hCG Detection

A control line was formed in the same manner as Example 1, except that a 1.0 mg/ml anti-IgG polyclonal antibody solution (50 mM $KH_2PO_4$, pH 7.2) was applied in an amount of about 1.0 μl/cm using the dispenser. The resulting membrane was then dried at 50° C. for 30 minutes to prepare a porous membrane pad for hCG detection.

Production of Conjugation Pad for hCG Measurement

A conjugation pad for hCG measurement was prepared in the same manner as in Example 1, except that only an hCG detection reagent was uniformly applied as a detection reagent (i.e., without applying a control line detection reagent).

hCG Measurement Using hCG Test Pieces

Figure 4:
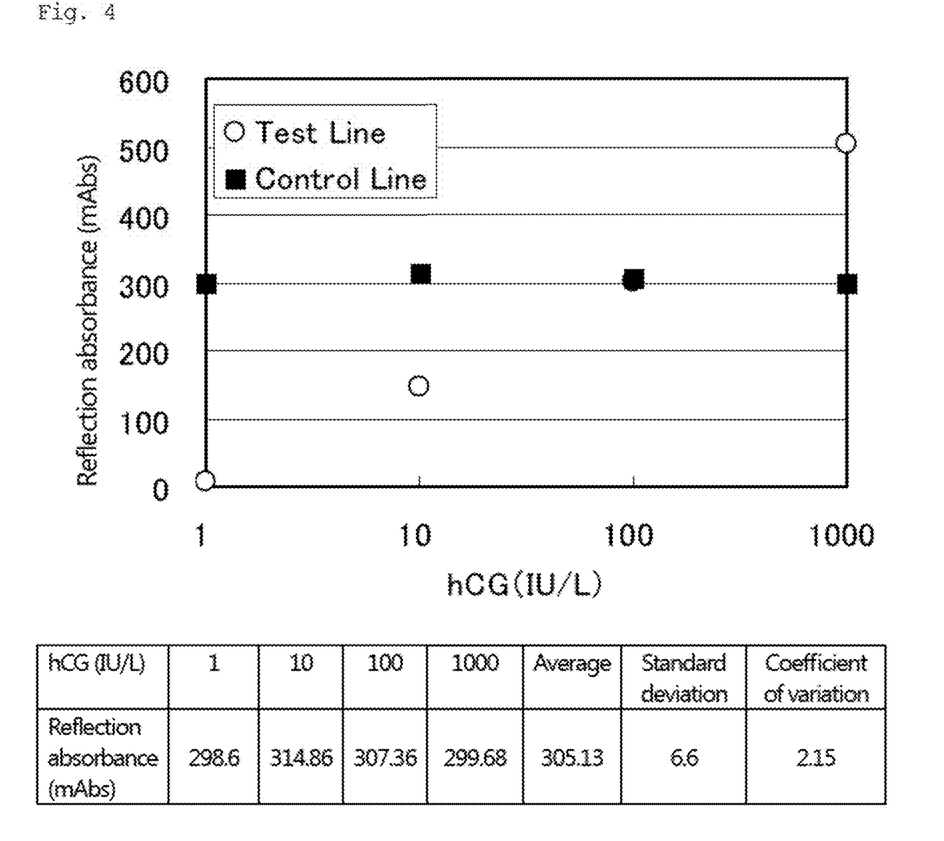
FIG. 4 shows the dilutional linearity in the results of measuring human chorionic gonadotropin (hCG) using the immunochromatographic test pieces of the present invention.

Using test pieces for hCG measurement produced by using the porous membrane pad and the conjugation pad prepared above, hCG was measured in the same manner as in Example 1. FIG. 4 shows a photograph taken 10 minutes after each sample was added dropwise. The intensity of color development on the test lines increased depending on the hCG concentration. The intensity of color development on the control lines decreased as the hCG concentration increased.

Quantification of hCG Using hCG Test Pieces

Figure 5:
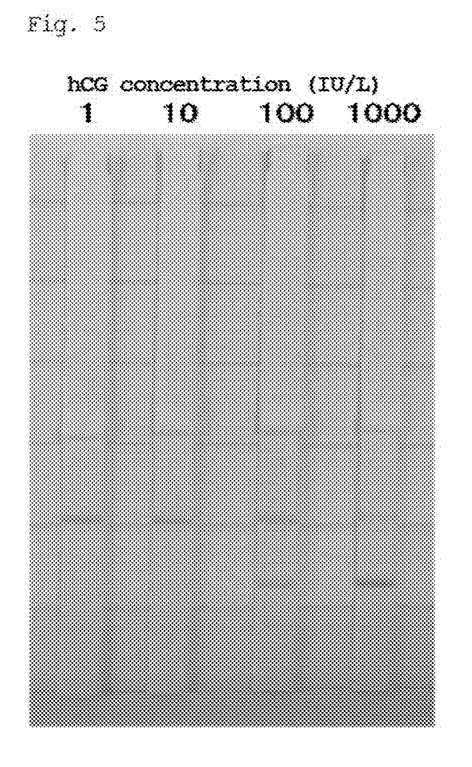
FIG. 5 is a photograph of the results obtained by measuring human chorionic gonadotropin (hCG) using conventional immunochromatographic test pieces.
Figure 6:
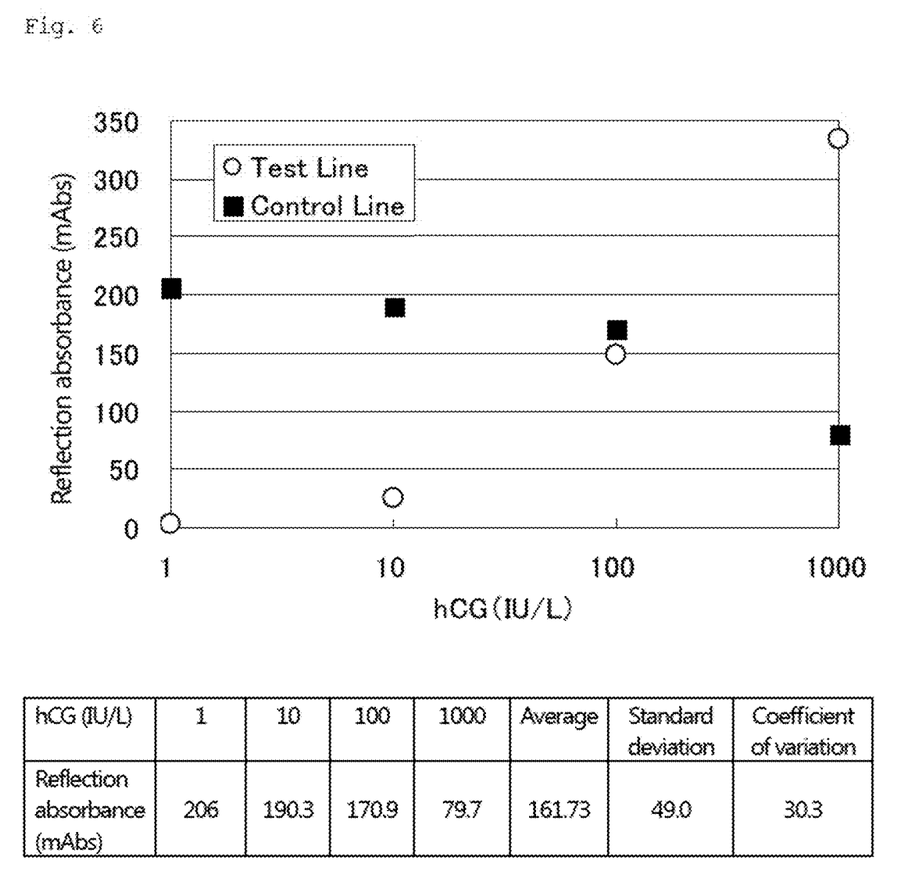
FIG. 6 shows the dilutional linearity in the results of measuring human chorionic gonadotropin (hCG) by using the conventional immunochromatographic test pieces.

The intensity of color development on the test pieces for hCG measurement was measured using an immunochromatographic reader in the same manner as in Example 1. FIG. 5 shows the results. The color density of the test lines increased in a manner dependent on the hCG concentration. The reflection absorbance of the control lines decreased from about 200 mAbs to 80 mAbs as the hCG concentration increased. The coefficient of variation in intensity of color development was 30.3%.

INDUSTRIAL APPLICABILITY

According to the present invention, a convenient immunochromatographic test piece with high measurement accuracy can be provided.

DESCRIPTION OF REFERENCE NUMERALS

1. Porous membrane pad
2. Sample pad
3. Conjugation pad
4. Absorbent pad
5. Test line
6. Control line
7. Adhesive sheet

The invention claimed is:

1. An immunochromatographic test piece for quantifying an analyte in a biological sample, the immunochromatographic test piece comprising:
   a) a conjugation pad impregnated with (1) a detection reagent that specifically binds to the analyte, and (2) a control line detection reagent, and
   b) a porous membrane pad on which an antibody for capturing the analyte is immobilized upstream, and an antibiotin antibody for specifically capturing the control line detection reagent is immobilized downstream,
   wherein the control line detection agent comprises detection particles having a biotin-labelled protein bound thereto, and the protein is a blocking peptide fragment consisting of the amino acid sequence of SEQ ID NO: 1, and
   wherein the detection particles are gold colloid particles or latex particles.

2. A method for quantifying an analyte in a biological sample, the method comprising using the immunochromatographic test piece according to claim 1.

3. An immunochromatographic analysis kit comprising the immunochromatographic test piece according to claim 1, a sample diluent, and an analyzing device.

4. The immunochromatographic test piece of claim 1, wherein the analyte is human chorionic gonadotropin (hCG).

* * * * *

SEQUENCE LISTING

```
<160> NUMBER OF SEQ ID NOS: 1

<210> SEQ ID NO 1
<211> LENGTH: 189
<212> TYPE: PRT
<213> ORGANISM: Escherichia coli

<400> SEQUENCE: 1

Pro Thr Lys His Ser Gln Val Phe Ser Thr Ala Glu Asp Asn Gln Ser
1               5                   10                  15

Ala Val Thr Ile His Val Leu Gln Gly Glu Arg Lys Arg Ala Ala Asp
            20                  25                  30

Asn Lys Ser Leu Gly Gln Phe Asn Leu Asp Gly Ile Asn Pro Ala Pro
        35                  40                  45

Arg Gly Met Pro Gln Ile Glu Val Thr Phe Asp Ile Asp Ala Asp Gly
    50                  55                  60

Ile Leu His Val Ser Ala Lys Asp Lys Asn Ser Gly Lys Glu Gln Lys
65                  70                  75                  80

Ile Thr Ile Lys Ala Ser Ser Gly Leu Asn Glu Asp Glu Ile Gln Lys
                85                  90                  95

Met Val Arg Asp Ala Glu Ala Asn Ala Glu Ala Asp Arg Lys Phe Glu
            100                 105                 110

Glu Leu Val Gln Thr Arg Asn Gln Gly Asp His Leu Leu His Ser Thr
        115                 120                 125

Arg Lys Gln Val Glu Glu Ala Gly Asp Lys Leu Pro Ala Asp Asp Lys
    130                 135                 140

Thr Ala Ile Glu Ser Ala Leu Thr Ala Leu Glu Thr Ala Leu Lys Gly
145                 150                 155                 160
```

-continued

```
Glu Asp Lys Ala Ala Ile Glu Ala Lys Met Gln Glu Leu Ala Gln Val
            165                 170                 175

Ser Gln Lys Leu Met Glu Ile Ala Gln Gln His Ala
            180                 185
```